United States Patent [19]

Biola et al.

[11] 4,005,114
[45] Jan. 25, 1977

[54] DISTILLATION OF PROPYLENE OXIDE FROM PROPYLENE OXIDATION REACTION PRODUCT IN MIXTURE WITH A PHOSPHORIC ACID ESTER

[75] Inventors: Georges Biola, Venissieux; Alain Fabre, Meyzieu; Gérard Schneider, Caluire, all of France

[73] Assignee: Rhone-Poulenc Industries, Paris, France

[22] Filed: Feb. 3, 1975

[21] Appl. No.: 546,443

[30] Foreign Application Priority Data

Feb. 11, 1974 France .............................. 74.05094

[52] U.S. Cl. ........................... 260/348.5 L; 203/60
[51] Int. Cl.[2] ....................................... C07D 301/02
[58] Field of Search .... 260/348 R, 348 C, 348.5 R, 260/348.5 L; 203/60, 71, 12, 14, 6, 8, 64, 69, 56; 208/48 AA

[56] References Cited

UNITED STATES PATENTS

| | | | |
|---|---|---|---|
| 2,903,465 | 9/1959 | Suter | 203/69 |
| 3,206,377 | 9/1965 | Cornell et al. | 203/60 |
| 3,391,063 | 7/1968 | Sennewald et al. | 203/71 |
| 3,578,568 | 5/1971 | Washall | 203/64 |
| 3,715,284 | 2/1973 | Burns et al. | 203/56 |
| 3,800,002 | 3/1974 | Chikatsu et al. | 208/48 AA |

Primary Examiner—Frank W. Lutter
Assistant Examiner—Frank Sever
Attorney, Agent, or Firm—Bacon & Thomas

[57] ABSTRACT

Propylene oxide is separated from the crude reaction product resulting from the oxidation of propylene, which separation is effected by distilling said reaction product in the presence of a neutral ester of phosphoric acid.

10 Claims, 1 Drawing Figure

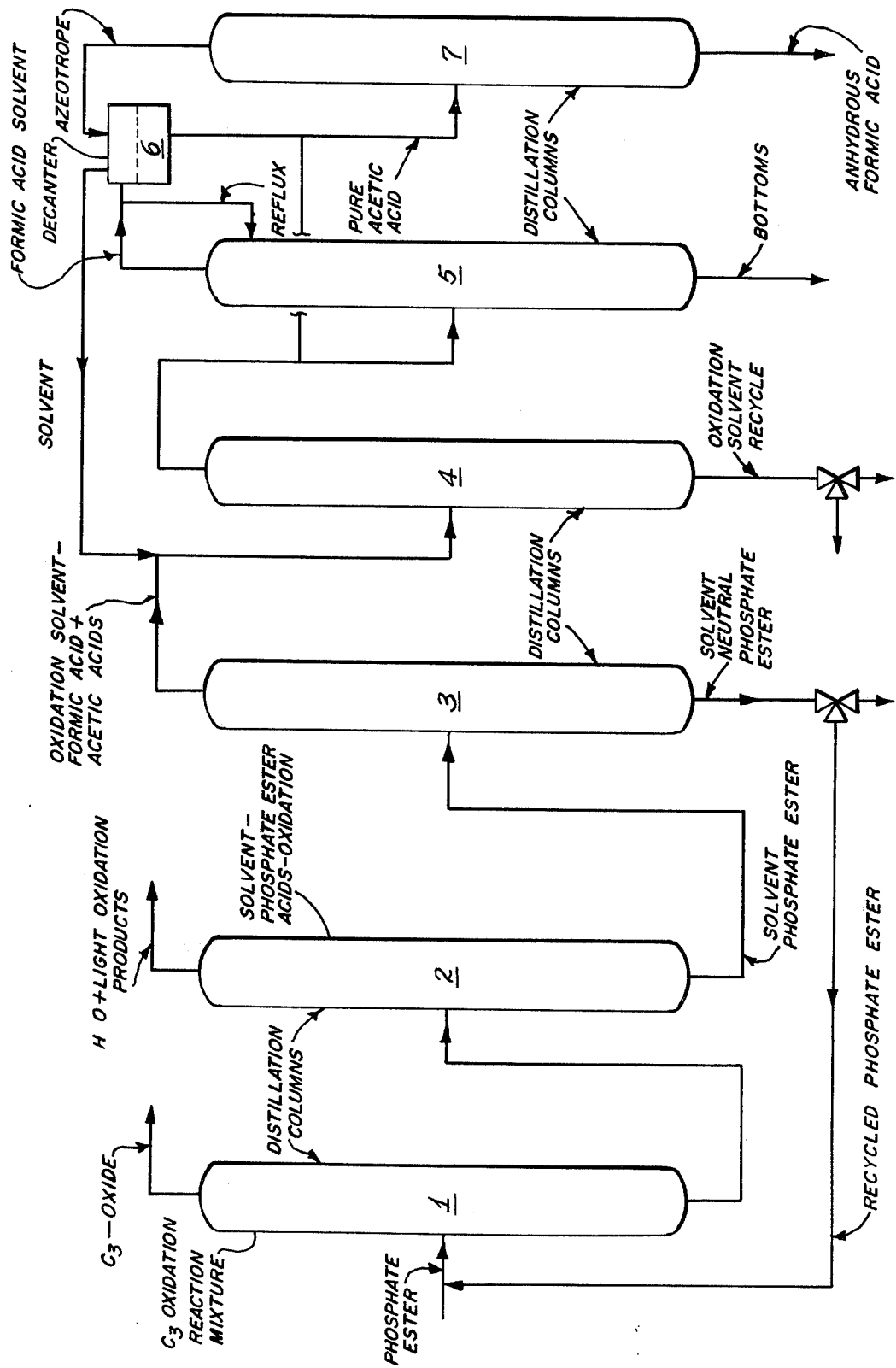

DISTILLATION OF PROPYLENE OXIDE FROM PROPYLENE OXIDATION REACTION PRODUCT IN MIXTURE WITH A PHOSPHORIC ACID ESTER

BACKGROUND OF THE INVENTION

1. Field of the Invention

The present invention relates to a method for the separation of propylene oxide from reaction mixtures comprising the same resulting from the oxidation of propylene with any one of the conventional oxidizing agents, e.g., air or molecular oxygen. More especially, the invention relates to the separation of propylene oxide for such reaction mixtures by distilling the same in the presence of a neutral ester of phosphoric acid.

2. Description of the Prior Art

It is a well known phenomenon in the state of the art that during the oxidation, or perhaps more correctly the epoxidation of propylene, a variety of by-products are simultaneously formed, certain of which markedly interfere with the ultimate yields to be attained by reason of their propensity of reaction with the desired propylene oxide end product. Thus, it is known, for example, that formic acid, and to a lesser extent, acetic acid, rapidly react with the epoxides. Compare H. W. Gibson, *Chem. Rev.*, 5, 675 (1969); W. J. Hickinbottom et al., *J. Chem. Soc.*, 4200 (1954). Such reaction is more pronounced in the case of propylene oxide, especially in the presence of small amounts of water, giving rise to the production of propylene glycol and certain esters thereof, as well as certain higher molecular weight products, such as the polypropylene glycols which usually are to some extent esterified. This type of reaction is especially pronounced during the separation, by simple distillation procedures, of fractions rich in the desired propylene oxide resulting from the liquid or condensed reaction mixtures emanating from a typical propylene oxidation. The ultimate result of course is a considerable loss of desired, initially produced epoxide.

And steps have been taken in the art to obviate the aforesaid difficulties by conducting the distillation of the propylene oxide admixture in the presence of certain additives which tend to minimize or oppose the reaction between the desired epoxide compound and the noted organic acids. According to U.S. Pat. No. 3,715,284, for example, the propylene oxide is distilled upon addition to the crude oxidation product or admixture, of acetone, optionally admixed with methanol. Such additives are employed to effect a physical separation, in the distillation column, of the propylene oxide from the noted acid and thus render impossible the competing, undesirable reactions. It has also been proposed to add an ester, for example, ethyl acetate, to the reaction medium to be treated. See French Pat. No. 2,018,290. However, this latter type of process necessitates the utilization of certain additives, the boiling points of which must be between the boiling point of propylene oxide and those of the noted acids. Consequently, in order to recycle any such additive, it of course is necessary to distill it in its entirety. This latter type of operation too is required for recovery of the acids. In sum, the end result is a significant energy requirement.

SUMMARY OF THE INVENTION

It has now suprisingly been found that the foregoing disadvantages of the prior art can be avoided, especially the competing reaction between the epoxide and any organic acid, notably formic acid, and which concomitantly provides for the substantially complete recovery of the propylene oxide, per se, initially present in the oxidation mixture, by utilization of certain additives having a boiling point which is higher than that of any of the products to be separated.

More particularly according to the invention, the fraction rich in the desired propylene oxide is distilled from a reaction mixture resulting from the oxidation of propylene in the presence of a neutral ester of phosphoric acid. These esters are maintained in the liquid phase and there the organic acids also are retained. It is supposed that, albeit we do not wish to be bound by such theoretical explanation, the said neutral esters of phosphoric acid complex the objectionable acids, particularly formic acid, and hence absolutely prevent same from reacting with the propylene oxide desired product.

BRIEF DESCRIPTION OF THE DRAWING

The FIGURE of drawing is a diagrammatic representation of the apparatus utilized in effecting the separation according to the invention.

DETAILED DESCRIPTION OF THE INVENTION

The novel process according to the invention is generally applicable to any crude reaction mixture resulting from the oxidation of propylene with a wide variety of oxidizing agents, such as air or molecular oxygen, the typical peroxides, peracids and derivatives thereof, the typical organic hydroperoxides, and the like, in either the liquid or vapor phase, and either in the presence or absence of suitable, conventional oxidation catalysts. For purposes of description only, the invention will be more fully described in the context of an oxidation procedure utilizing either air or molecular oxygen, in the liquid phase, utilizing any suitable reaction solvent, and without intent that such exemplary description be considered as in any way limiting the scope of this invention.

By "neutral ester" of phosphoric acid, there is intended those esters of the following structural formula:

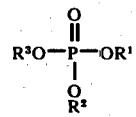

wherein $R^1$, $R^2$ and $R^3$ may be the same or different and are independently selected from the group consisting of lower alkyl having from 1 to 8 carbon atoms, phenyl and alkylphenyl with one or two alkyl groups having from 1 to 3 carbon atoms. Such esters can be employed either alone or in various admixtures, and one readily available commercial product is tri-n-butyl phosphate.

The amount of the phosphoric acid neutral ester which can be employed varies over very wide limits. Generally, it is preferred to employ at least one mole of the neutral ester for each mole of, for example, formic acid present in the reaction mixture to be separated. It is more preferred to use an excess of ester up to, for example, 10 moles of ester per mole of formic acid. The neutral ester of phosphoric acid can be introduced separately into the distillation vessel, or it can be already present in the reaction mixture to be distilled, namely, prior to introduction into the distillation column.

The distillation procedure itself does not require any particular operating procedure, and the distillation conditions, which are more or less a mere function of the particular composition to be distilled, would be readily apparent to the skilled worker in the art. The principle caution, however, to be taken into account is to avoid conditions such as would lead to a temperature increase in the vessel which would be in excess of the degradation temperature of the phosphoric acid ester. Also, a pressure parameter is accordingly introduced into this temperature equation.

The resulting distillate according to the invention principally comprises the desired propylene oxide separated from the oxidation reaction mixture, certain low-boiling impurities such as methyl formate, acetaldehyde, other oxygenated by-products and, optionally, unreacted propylene. The distillate can be treated according to the usual techniques in the art, for example, by extractive distillation, for the recovery of propylene oxide in a pure state.

According to another desirable embodiment of the present invention, the unreacted propylene can be separated from the oxidation mixture prior to the distillation of same, as aforesaid. The liquid phase or distilland which constitutes the non-distilled fraction of the oxidation mixture principally contains, other than the phosphoric acid ester additive, formic and acetic acids, oxygenated by-products and, optionally, the solvent employed for the oxidation reaction and a small amount of water produced during the reaction.

It has also been found according to the invention that the presence of the neutral phosphate provides for an added advantage in the dehydration of that liquid phase remaining upon distillation of the fraction rich in the propylene oxide, and which permits of the separate recovery, under facile conditions, of the formic and acetic acids in anhydrous state, as well as for the separate recovery of the solvent of oxidation. Indeed, it is well known that water, formic acid and a large amount of the solvent employed for the oxidation of propylene, and in particular the typical aromatic hydrocarbon reaction solvents, such as benzene or the chlorobenzenes, normally distill in the form of a heterogeneous ternary azeotrope. But it has now been determined that in the presence of a neutral ester of phosphoric acid, such hetero-azeotrope is broken. Thus, one can readily dehydrate the reaction medium by distillation of appreciable quantities of formic and acetic acids. Next according to the invention these acids can readily be separated with the oxidation solvent and, similarly, the neutral ester of phosphoric acid can be recycled to the initial distillation of the fraction rich in the propylene oxide. Then the binary azeotrope which is formed between the formic acid and the solvent of oxidation is utilized to permit of the separate recovery of anhydrous formic and acetic acids.

Referring specifically to the single FIGURE of drawing to more fully illustrate the various principles of this invention, a distillation column 1 is charged with a reaction mixture resulting from the oxidation of propylene, and to which has been added a suitable quantity of the neutral ester of phosphoric acid. Overhead, a propylene oxide enriched fraction is recovered which is fed to suitable apparatus [not shown] for the recovery of pure propylene oxide. The non-distilled fraction of this mixture is passed to the head of column 2 where there is removed, principally, water and light oxidation products such as alcohols or acetone. The dehydrated liquid supplies the column 3 where there is drawn off effluent essentially comprised of the said neutral ester of phosphoric acid and which can be recycled to the distillation column 1. The distillate is a mixture essentially comprising the solvent of oxidation and the formic and acetic acid fraction. This distillate is fed to the column 4, as illustrated, and at the head of which column there is separated a fraction comprising the noted formic and acetic acids and a certain amount of the solvent of oxidation. The greater proportion of the solvent which remains as a bottoms product of this distillation is recycled to the propylene oxidation. The overhead fraction from the column 4 is supplied to the column 5 whereat a formic acid/solvent azeotrope distills at the head and separates into two phases in the vessel 6. Essentially pure acetic acid is recovered from the bottom of this vessel. The upper, settled phase, rich in solvent, is returned to the columns 5 and/or 4. The lower phase passes to the column 7, at the base of which there is drawn off the anhydrous formic acid. The distilled fraction, comprising the formic acid/solvent azeotrope is fed to the settling tank 6. A portion of the lower phase in the vessel 6 can thence be fed to the column 5 to enrich the feed in formic acid. Drainage can be effected at the base of the columns 3 and/or 4 in order to prevent an increase in the concentration of the high molecular weight or heavy impurities, such as the polypropylene glycols in the distillation cycle and/or oxidation reactor.

Respecting the actual working conditions in the aforesaid various distillation steps, the only criticality exists at those phases in the cycle whereat the phosphoric acid ester is present and comprises, as hereinbefore mentioned, maintaining the temperature at these points in the system below the degradation temperature of the neutral ester. Thus, in certain instances, for example, the column 3 must be maintained under a reduced pressure to accomplish the above aim and whereat the distillation is conducted on a mixture containing the organic phosphate in a major proportion.

In order to more fully illustrate the present invention and the advantages thereof, the following specific examples are given, it being understood that the same are intended and included as being illustrative and in no wise limitative.

EXAMPLE 1

There were continuously introduced, to approximately the middle of an Oldershaw column having 20 plates, 1900 g/hour of liquid preheated to 45° C. comprising 0.33 parts by weight of tributyl phosphate per 1 part by weight of a mixture resulting from the oxidation of propylene with air, in liquid phase, in the presence of monochlorobenzene solvent, and having the following composition in % by weight.

| | |
|---|---|
| Propylene | 2.9 |
| Propylene oxide | 4.84 |
| Methyl formate | 0.53 |
| Acetaldehyde | 0.43 |
| Various oxygenated products (propanol, acetone, acrolein, isopropanol, allyl alcohol, allyl and isopropyl formate) | 2.33 |
| Formic acid | 3.12 |
| Acetic acid | 1.85 |
| Propylene glycol monoformate | 0.11 |
| Propylene glycol diformate | 0.15 |
| Propylene glycol (PGL) | 0.18 |

-continued

| | |
|---|---|
| Water | 0.56 |
| Monochlorobenzene | 83 |

The column was operated under atmospheric pressure; the boiler temperature was 121°–122° C. and that of the head vapors was 34°–35° C. There were recovered 134.1 g/h of a head fraction (i.e., 7.06% of the feed weight) and 1765.9 g/h of bottoms.

The composition by weight of these fractions is reflected in the following Table I:

Table I

| Product | Head fraction (in %) | Bottom fraction (in %) |
|---|---|---|
| Propylene | 30.8 | 0.01 |
| Propylene oxide | 51.3 | |
| Methyl formate | 5.6 | |
| Acetaldehyde | 3.4 | 0.09 |
| Miscellaneous | 8.8 | 1.21 |
| Formic acid | | 2.52 |
| Acetic acid | | 1.49 |
| PGL monoformate | | 0.09 |
| PGL diformate | | 0.12 |
| Propylene glycol | | 0.14 |
| Water | | 0.45 |
| Monochlorobenzene | | 67 |
| Tri-n-butyl phosphate | | 26.90 |

It should be noted that substantially no propylene oxide was degraded, since the quantity recovered represented 99.7% of the epoxide present in the charge to be distilled.

EXAMPLE 2

In a distillation column identical to that utilized in the previous Example 1, there were introduced 1833 g/hour of a mixture resulting from the oxidation of propylene with air, in liquid phase, in the presence of monochlorobenzene solvents and to which was added tri-butyl phosphate. The liquid was at a temperature of 56° C. The composition in % by weight was as follows:

| | |
|---|---|
| Propylene | 0.70 |
| Propylene oxide | 2.91 |
| Methyl formate | 0.18 |
| Acetaldehyde | 0.25 |
| Various products (propanol, acetone acrolein, isopropanol, allyl alcohol, isopropyl and alkyl formates) | 1.14 |
| Formic acid | 1.77 |
| Acetic acid | 0.67 |
| Propylene glycol | 0.67 |
| Water | 0.35 |
| Monochlorobenzene | 72.9 |
| Tributyl phosphate | 18.5 |

The column operated under normal pressure, with a boiler temperature of 127° C. and a head temperature of 35° C.; the reflux ratio was 10/1.

There were recovered 86 g/h of a head fraction (that is, 4.69% by weight of the feed) and 1744 g at the bottom of the column.

The compositions by weight of these fractions are given in the following Table II:

Table II

| Product | Head fraction (in %) | Bottom fraction (in %) |
|---|---|---|
| Propylene | 12.1 | |
| Propylene oxide | 61.7 | 0.005 |
| Methyl formate | 5.6 | 0.01 |
| Acetaldehyde | 4.8 | 0.03 |
| By-products | 15.7 | 0.74 |
| Formic acid | | 1.84 |
| Acetic acid | | 0.70 |
| Propylene glycol | | 0.63 |
| Water | | 0.35 |
| Monochlorobenzene | | 76.3 |
| Tributyl phosphate | | 19.4 |

99.8% of propylene oxide was recovered.

In comparison, a distillation was carried out under conditions identical with those of the previous example, but in the absence of tributyl phosphate.

The recovered head fraction represented 4.39% by weight of the feed. The composition by weight of the head fraction and the distillation bottoms are given in the following Table III:

Table III

| Product | Head fraction (in %) | Bottom fraction (in %) |
|---|---|---|
| Propylene | 19.5 | |
| Propylene oxide | 51.9 | |
| Methyl formate | 5.1 | |
| Acetaldehyde | 6.9 | |
| Oxygenated by-products | 16.6 | 0.72 |
| Formic acid | | 0.71 |
| Acetic acid | | 0.74 |
| Propylene glycol + esters | | 1.72 |
| Water | | 0.47 |
| Monochlorobenzene | | 95.63 |

It can be seen that only 63.9% of the feed propylene oxide was recovered. Similarly, a formic acid loss of about 69.2% is noted, which indicates a reaction between the propylene oxide and formic acid to yield products such as propylene glycol or polypropylene glycol esters.

EXAMPLE 3

In a column identical to that utilized in the previous examples, there were introduced 1473.5 g/h of the product of oxidation of propylene with air, in liquid phase, in monochlorobenzene solvent, and 373.4 g/h of tributyl phosphate at a temperature of 57° C.

The composition by weight in % of the oxidation product was as follows:

| | |
|---|---|
| Propylene | 0.86 |
| Propylene oxide | 3.35 |
| Methyl formate | 0.20 |
| Acetaldehyde | 0.27 |
| Oxygenated by-products | 1.31 |
| Formic acid | 2.01 |
| Acetic acid | 0.79 |
| Propylene glycol | 0.32 |
| Water | 0.39 |
| Monochlorobenzene | 90.6 |

The column operated under normal pressure, at a bottom temperature of 128° C. and a head temperature of 34° C.; the reflux ratio was 10/1.

77.9 g/h of head fraction and 1769 g/h of bottoms were recovered.

The compositions by weight of these fractions are given in the following Table IV:

Table IV

| Product | Head fraction (in %) | Bottom fraction (in %) |
|---|---|---|
| Propylene | 15.5 | |
| Propylene oxide | 63.5 | 0.01 |
| Methyl formate | 4.5 | |
| Acetaldehyde | 4.5 | 0.03 |
| Oxygenated by-products | 11.8 | 0.78 |
| Formic acid | | 1.76 |
| Acetic acid | | 0.65 |
| Propylene glycol | | 0.27 |
| Water | 0.2 | 0.27 |
| Monochlorobenzene | | 74.92 |
| Tributyl phosphate | | 21.24 |

Propylene oxide was quantitative recovered, with more than 99.5% in the head fraction.

EXAMPLE 4

This example was carried on in an apparatus of the type described in the figure of drawing. The parts and percentages are given by weight.

The column 1 was charged with 274.7 parts/hour of a mixture comprising about 82.3% of monochlorobenzene, 8.7% of tributyl phosphate and by-products resulting from propylene oxidation. This mixture was comprised of the reaction medium resuting from the oxidation of propylene with air, in liquid phase, in monochlorobenzene solvent, from which the unreacted propylene was removed, and to which tributyl phosphate was added. The column 1 operated under a pressure of 1 atmosphere at 34° C. at the head of the column and 127° C. at the base. There were recovered as overheads 11.5 parts/h of a fraction rich in propylene oxide containing acetaldehyde and methyl formate. This fraction was treated in a purification zone [not shown] where 10 parts/h of pure propylene oxide, 0.8 part/h of methyl formate and 0.7 part/h of acetaldehyde were separated.

The liquid drawn off at the bottom of column 1, namely, 263.2 parts/h, comprising 86% of monochlorobenzene, 9.1% of tributyl phosphate, about 2% of formic and acetic acids, minor amounts of water and oxygenated by-products, was fed to column 2, provided at its top with a decanter [not shown] and operating under 1 atmosphere at 90° C. at the head of the column and 135° C. at the bottom thereof. The head fraction, condensed and settled into two layers. The lower phase was returned to column 2 as reflux while the upper phase, comprising 5.5 parts/h and containing essentially water, alcohols and light carbonylated compounds were drawn off.

The distillation bottoms were charged to column 3 operating under 200 mm Hg, at 136° C. in the boiler and 88° C. at the head. There were recovered as bottoms 26.3 parts/h of a liquid containing 91.4% tributyl phosphate and monochlorobenzene.

The condensed head vapors, comprised of 96.8% of monochlorobenzene, 1.5% of formic acid, 0.8% of acetic acid and byproducts, were fed at a rate of 231.4 parts/h, to the column 4 operating under normal pressure at 136° C. at the bottoms where there were recovered 226.3 parts/h of a liquid rich in solvent which could be returned to the oxidation reactor.

The head fraction of column 4 was fed into the column 5, together with additional liquid rich in formic acid emanating from the lower phase of the decanter 6. The liquid supplying the column 5, overall, was 10.4 parts/h. The pressure was 1 atmosphere, the temperature was 95° C. at the head of the column and 120° C. at the base. 1.76 part/h of acetic acid with a purity greater than 99.9% was recovered.

The fraction of the lower phase of decanter 6 which was not fed to 5, was charged to column 7 operating under 1 atmosphere, 95° C. at the head of the column and 102° C. at the base. 3.38 parts/h of formic acid with a purity of 99.9% was recovered.

4.1 parts/h of the upper phase of decanter 6 were returned to column 4, the remainder being fed to column 5 as reflux.

While there have been described and pointed out the fundamental novel features of the invention as applied to the preferred embodiments, those skilled in the art will appreciate that various modifications, changes, and omissions in the separation of propylene oxide from propylene oxidation reaction product illustrated and described can be made without departing from the spirit of the invention. It is the intention, therefore, to be limited only by the scope of the following claims.

What is claimed is:

1. A method for the separation of propylene oxide from the reaction mixture resulting from the oxidation of propylene, which method comprises adding a neutral ester of phosphoric acid having the structural formula:

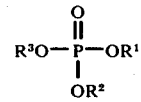

wherein $R^1$, $R^2$ and $R^3$ may be the same or different and are independently selected from the group consisting of lower alkyl having 1 to 8 carbon atoms, phenyl and alkylphenyl with one or two alkyl groups having from 1 to 3 carbon atoms to said reaction mixture and distilling said reaction mixture to recover a propylene oxide enriched distillate and a distilland.

2. The method as defined by claim 1, wherein the oxidation of propylene is conducted in liquid phase.

3. The method as defined by claim 2 further comprising separately recovering solvent of reaction from the distilland.

4. The method as defined by claim 2, wherein the liquid phase comprises a monochlorobenzene solvent of reaction.

5. The method as defined by claim 1, wherein the neutral ester is tri-n-butyl phosphate.

6. The method as defined by claim 1, further comprising separately recovering formic and acetic acids from the distilland.

7. The method as defined by claim 1, further comprising separately recovering the neutral phosphate from the distilland.

8. The method as defined by claim 7, further comprising recycling the neutral phosphate to the distillation zone.

9. Apparatus for the separation of propylene oxide as defined by claim 1, which apparatus comprises a first distillation vessel for receiving a charge of said reaction product and said neutral ester of phosphoric acid and distilling said reaction product whereby an overhead propylene oxide enriched fraction and a first distilland fraction is produced, means for recovering pure propylene oxide from said overhead propylene oxide enriched fraction, means for feeding said first distilland to a second distillation vessel whereby a second distillation is conducted producing an overhead fraction and a second distilland, means for passing said second distilland to a third distillation vessel whereby a third distillation is conducted producing an overhead fraction and a third distilland, means for recycling said third distilland to said first distillation vessel, means for passing the overhead fraction obtained from said third distillation vessel to at least one subsequent distillation vessel and at least one separatory vessel associated therewith comprising means for separating the third distillation vessel distillate into the individual components thereof.

10. The apparatus as defined by claim 9, further comprising means for recovering the said second distillation vessel distillates.

* * * * *